United States Patent [19]

Mukaida et al.

[11] Patent Number: 5,716,707
[45] Date of Patent: Feb. 10, 1998

[54] WATER ABSORBENT COMPOSITON AND MATERIAL

[75] Inventors: Shingo Mukaida; Kazuhiko Iguchi, both of Kyoto-fu; Kenji Tanaka, Shiga-ken, all of Japan

[73] Assignee: Sanyo Chemical Industries, Ltd., Kyoto-fu, Japan

[21] Appl. No.: 782,031

[22] Filed: Jan. 15, 1997

Related U.S. Application Data

[63] Continuation of Ser. No. 526,194, Sep. 11, 1995, which is a continuation of Ser. No. 193,378, Jan. 26, 1994, abandoned.

[30] Foreign Application Priority Data

Feb. 24, 1993 [JP] Japan ..................... 5-61143
Feb. 24, 1993 [JP] Japan ..................... 5-61144

[51] Int. Cl.$^6$ ..................... C08J 3/12; A61L 15/60
[52] U.S. Cl. ..................... 428/402; 428/407; 525/54.31; 525/54.32; 525/57; 525/58; 525/207; 525/221; 525/218
[58] Field of Search ..................... 428/402, 407; 525/54.31, 54.32, 57, 58, 207, 221, 218

[56] References Cited

U.S. PATENT DOCUMENTS

| | | | |
|---|---|---|---|
| 4,076,663 | 2/1978 | Masuda et al. | 525/54.31 |
| 4,093,776 | 6/1978 | Aoki et al. | 428/402 |
| 4,102,842 | 7/1978 | Fujimoto et al. | 524/555 |
| 4,647,504 | 3/1987 | Kimimura et al. | 428/327 |
| 4,781,966 | 11/1988 | Taylor et al. | 428/152 |
| 4,790,839 | 12/1988 | Ahr | 604/367 |
| 4,840,692 | 6/1989 | Kamstrup-Larsen | 156/252 |
| 4,939,030 | 7/1990 | Tsuji et al. | 428/315.5 |
| 4,977,211 | 12/1990 | Doi et al. | 525/54.31 |
| 5,115,035 | 5/1992 | Shiraki et al. | 525/314 |
| 5,143,680 | 9/1992 | Molnar et al. | 264/511 |
| 5,156,902 | 10/1992 | Pieper et al. | 428/206 |
| 5,236,427 | 8/1993 | Hamajima et al. | 604/378 |
| 5,295,986 | 3/1994 | Zehner et al. | 604/385.1 |
| 5,340,853 | 8/1994 | Chmelir et al. | 524/56 |
| 5,360,419 | 11/1994 | Chen et al. | 604/374 |
| 5,360,845 | 11/1994 | Billmers et al. | 524/51 |

FOREIGN PATENT DOCUMENTS

| | | |
|---|---|---|
| 22 22 780 | 5/1972 | Germany. |
| 30 02 136 | 1/1980 | Germany. |
| 2-242858 | 9/1990 | Japan. |
| WO 91/18042 | 11/1991 | WIPO. |

OTHER PUBLICATIONS

*Encyclopedia of Polymer Science and Engineering*, Suppl. vol., Acid-Base Interactions to Vinyl Chloride Polymers, John Wiley & Sons, New York, p. 862.

*Primary Examiner*—Kathleen Choi
*Attorney, Agent, or Firm*—Merchant, Gould, Smith, Edell, Welter & Schmidt, P.A.

[57] ABSTRACT

The present invention relates to a water absorbent composition comprising 100 parts by weight of water absorbing polymer particles and 0.5 to 30 parts of a resin powder having heat adhesion property at 50°–200° C. The present invention also relates to a water absorbing material and water absorbing products using the said water absorbing material comprising the water absorbing polymer particles, a resin having heat adhesion property at 50°–200° C. and fibrous material, wherein the water absorbing polymer particles are adhered to the fibrous material through the resin by heat treatment at temperature exceeding the temperature exhibits heat adhesion property of the resin. The water absorbent composition of the present invention provides excellent adhesion to a fibrous material, while it maintains the water absorbency of the original water absorbing polymer, and is consequently useful as raw material for sanitary goods such as disposable diapers and sanitary napkins etc. The water absorbing material of the present invention has excellent water absorbency, absorbing speed and shape retention property after water absorption. Consequently, it is useful for water absorptive goods such as disposable diapers and sanitary napkins.

4 Claims, No Drawings

WATER ABSORBENT COMPOSITON AND MATERIAL

This is a continuation of application Ser. No. 08/526,194, filed Sep. 11, 1995, which is a continuation of Ser. No. 08/193,378, filed Jan. 26, 1994, now abandoned, which application(s) are incorporated herein by reference.

BACKGROUND OF THE INVENTION

1. Field of the Invention

The present invention relates to a water absorbent composition having excellent absorbency and excellent adhesion to fibrous material. It also relates to a water absorbing material in which water absorbent resin particles adhere to a fibrous base. More specifically, the present invention relates to a water absorbing material having excellent water absorbency, and excellent shape retention after water is absorbed.

2. Description of the Prior Art

Granular water absorbents which possesses water absorbing capacity for aqueous solutions, comprising hydrophilic crosslinked polymers called water absorbent resins, are known. Examples of these water absorbent resins include coplymers of starch-acrylic acid salts, crosslinked acrylic acid salts, crosslinked copolymers of acrylic acid and/or salts thereof with other monomers, copolymers of crosslinked isobutylene-maleic acid anhydride, copolymers of polyvinyl alcohol-(meth)acrylic acid, modified cellulose derivatives, modified polyethylene oxide, modified polyvinyl alcohol, and other types of polymers. They have been extensively employed in sanitary goods such as paper diapers, sanitary napkins, etc.

Combined with a fibrous base such as fluff pulp and/or synthetic fiber, granular water absorbing polymers as stated above have been used for paper diapers, sanitary napkins and other water absorbent goods.

These conventional granular water absorbing polymers possess excellent water absorbency, but they exhibit unsatisfactory adhesion to natural fiber such as fluff pulp, and also to synthetic fiber such as polyethylene fibers, polypropylene fibers, polyester fibers, and bicomponent fibers thereof. In particular, as the ratio of water absorbing polymer to fiber increases (for example, when the weight ratio of water absorbing polymer to fiber exceeds 30/70), the fixation between water absorbing polymers and fibers decreases, causing problems of displacement of the water absorbing polymers, localization of the water absorbing polymers, and separation of the polymer from fibers.

It has been proposed that the entire surface of the water absorbent be covered with slowly-water-soluble and/or hydrolyzable thermoplastic resins possessing adhesion property to fibers, etc. (Japanese Patent Application Laid-open No. 242858/1990). This improves the adhesion property to the fiber, but has the defect that the water absorbing properties which the water absorbing polymer originally possessed, in particular the water absorbing speed and the initial absorption rate, are excessively degraded. It is, therefore, difficult to apply the above proposal to sanitary goods such as disposable diapers and sanitary napkins, which require the capability to instantaneously absorb and retain discharged urine, menstrual blood, etc.

To combine water absorbing polymer particles (A) with fibrous materials (C), the usual method is to sandwith, wrap or blend the particles (A) with the fibrous material (C). These methods are not satisfactory, because the required adhesion cannot be achieved and the particles (A) tend to separate from the fibrous materials (C). In order to improve the adhesion of the particles (A) to the fibrous material (C), it has been proposed (1) to spray a small amount of water over the mixture of the particles (A) and the fibrous materials (C) in order to allow the surface of the polymer particles (A) to swell and the polymer particles (A) to adhere to the fibrous materials (C), and then to dry; (2) to spray a small amount of water over the fibrous materials (C), and then to sprinkle or blend the water absorbing polymer particles (A), and dry; or (3) to spray steam in place of water, and then to dry.

These methods (1), (2) and (3) have some adhesion-improving effects, but still do not provide a satisfactory level of adhesion. Moreover, as previously stated, in particular as the ratio of the water absorbing polymer particles to the fibrous materials increases (e.g. when the ratio of water absorbing polymers to fibers exceeds 30:70 by weight), the adhesion deteriorates. In addition, there is the problem that drying is required after the surface of the water absorbing polymer particles is brought in contact with water or steam to swell the polymer particle surface; this causes the surface condition of the water absorbing polymer particles (A) to change and results in a lowering of the water absorbing rate or lessening of the water absorbing capacity.

In an attempt to solve the above mentioned problems, the following methods have been proposed: (4) after applying adhesive to the surface of the fibrous materials (C), the water absorbing polymer particles (A) are adhered to it; and (5), after dispersing the water absorbing polymer particles (A) in a large volume of organic solvent in which the binder is dissolved and applying it to the fibrous materials (C) or dipping the fibrous materials (C) in it, it is heated and dried to evaporate the organic solvent. However in the Method (4), owing to the influence of the adhesive which did not participate in adhesion of the water absorbing polymer particles (A) to the fibrous materials (C), the fibrous materials adhere mutually, degrading the water absorbing efficiency of the water absorbing material obtained; and the stickiness makes it difficult to handle the material. In the Method (5), because the surface of the water absorbing polymer particle is covered with the binder, the water absorbing speed and the water absorbing efficiency are lessened. In addition, since a significant amount of energy is required to evaporate the organic solvent, the method is not only uneconomical but there is also a problem of safety owing to residual organic solvent.

SUMMARY OF THE INVENTION

In view of the problems mentioned above, the present inventors have intensively sought to develop a water absorbent composition which has excellent water absorbency (in particular, initial absorption rate) and fixation to fibrous material, and a water absorbing material which provides excellent water absorbency, and shape retention after water is absorbed.

According to the present invention, a water absorbent composition comprises water absorbing polymer particles (A) and resin powder (B) having heat adhesive property at 50° to 200 ° C., wherein the amount of the resin powder (B), per 100 parts by weight of the water absorbing polymer particles (A), is 0.5 to 30 parts by weight.

The present invention further comprehends a water absorbing material comprising water absorbing polymer particles (A), resin powder (B) having heat adhesive property at 50° to 200 ° C. and fibrous materials (C), wherein the water absorbing polymer particles (A) are affixed to the fibrous materials (C) via resin (B) by heat treatment at temperature exhibit heat adhesion property of the resin (B).

DETAILED DESCRIPTION OF THE INVENTION

Advantageously the water absorbing polymer particles (A) are hydrophilic crosslinked polymers which have an efficiency for absorbing water of about 30 to 1000 times of their own weight. They are not particularly limited by type of polymer and manufacturing method when the water absorbing polymer contains a hydrophilic group such as carboxylic acid (salt) group (i.e. a carboxylic acid group and/or carboxylate group). Sulfonic acid (salt) groups, phosphoric acid (salt) groups, tertiary amino groups, quaternary ammonium salt groups, hydroxyl groups or polyethylene oxide groups may be the prinicpal constituent unit. Examples of water absorbing polymers which can be preferably employed for the present invention include the copolymers of starch grafted-acrylic acid salts described in Japanese Patent Publication No. 46199/1978, crosslinked or self-crosslinked polyacrylic acid salt obtained by the reverse phased suspension polymerization described in Japanese Patent Publication No. 30710/1979 and Japanese Patent Application Laid Open No. 26909/1981, respectively, crosslinked polyacrylic acid salts obtained by aqueous-solution polymerization (adiabatic, thin-layered or spray polymerizations) described in Japanese Patent Application Laid Open No. 133413/1980, saponified copolymers of vinyl ester and unsaturated carboxylic acid or the derivatives thereof described in Japanese Patent Application Laid Open No. 14689/1977 and 27455/1977, respectively, water absorbent resin containing sulfonic acid groups or salts descrived in Japanese Patent Application Laid Open No. 2312/1983 and 36309/1986 respectively, crosslinked copolymers of isobutylene-maleic anhydride, hydrolyzates of crosslinked starch-acrylonitrile copolymer, crosslinked carboxymethyl cellulose derivatives, crosslinked polyethylene-oxide derivatives, crosslinked polyvinyl alcohol derivatives, and the partially hydrolyzed polyacrylamide. The water absorbing polymer whose surface is further crosslinked by closslinkers in the above-mentioned water absorbing polymer can also be used. Two or more types of the above water absorbing polymer may be used.

The water absorbency of the above mentioned water absorbing polymer for physiological saline solution aqueous solution of sodium chloride) is, in general, 30 times or more of its own weight, preferably 35–100 times, or still preferably 40–80 times.

The shape of the water absorbing polymer particles is not critical. They may be powder or particles which are paticulate, granular, pelletized, lamellar, lumpy, pearly or fine powdery. Water absorbing polymer particles having a size distribution such that 90 weight % or more of the particles have a size of 1 mm or smaller is preferable. More preferably, they are partculate, granular, pelletized, lamellar or lumpy water absorbing resin having a size distribution such that 90 weight % or more of the particles have a size of 0.1 mm to 0.9 mm.

Examples of the resin (B) in the present invention include polyolefin resin (e.g., polyethylene, polypropylene, low molecular weight polyethylene, low molecular weight polypropylene, etc.), polyolefin derivatives (e.g., polyethylene modified by maleic acid, chlorinated polyethylene, polypropylene modified by maleic acid, ethylene-acrylic acid copolmer, copolymer of ethylene-maleic acid anhydride, propylene-acrylic acid copolymer, copolymer of propylene-maleic acid anhydride, copolymer of isobutylene-maleic acid anhydride, maleic polybutadiene, ethylene-vinyl acetate copolymer and its maleic compounds), polyester type resin, polyamide type resin, polycaprolactam type resin, polystyrene resin and derivatives thereof (e.g., polystyrene, sulfonated polystyrene, copolymer of styrene-maleic acid anhydride, etc.), thermoplastic polyurethane resin, high molecular weight polyethylene glycol, vinyl acetate resin, waxes (e.g. paraffin wax, beeswax, beef tallow, etc.), long-chain fatty acid ester resin, and mixtures of two or more types of these materials. In addition, the resin generally called hot-melt type addhesives may be used for the present invention.

Among these examples, those preferred are low molecular polyolefin resin (e.g., low molecular polyethylene, low molecular polypropylene, etc.), polyolefine modified by carboxylic acid (e.g., polyethylene maleic acid, polypropylene modified by maleic acid, etc.), olefin-acrylic acid copolymer (e.g., ethylene-acrylic acid copolymer, propylene-acrylic acid copolymer, etc.), copolymer of olefin-maleic acid anhydride (e.g., copolymer of ethylene-maleic acid anhydride, copolymer of propylene-maleic acid anhydride, copolymer of isobutylene-maleic acid anhydride, etc.). Particularly preferable resins are polyethylene modified by maleic acid or polypropylene modified by maleic acid containing 1–30 weight % maleic acid component; ethylene-acrylic acid copolymer of propylene-acrylic acid copolymer containing 1–30 weight % of acrylic acid component; and copolymer of ethylene-maleic acid anhydride, copolymer of propylene-maleic acid anhydride or copolymer of isobutylene-maleic acid anhydride containing 1–30 weight % maleic acid anhydride component.

The resin (B) exhibit heat adhesion property at 50° to 200° C. can be used for this invention, and preferably the resin (B) having a melting point of 70° to 80° C. More preferably the melting point of the resin (B) is from 80° to 160° C. If the temperature showing adhesion property is below 50° C., problems such as blocking during storage of application of water absorbents or water absorbing material, or sticking of water absorbents each other, tend to occur. On the other hand, if the temperature exhibit heat adhesion property exceeds 200° C., high temperature is required to affix the water absorbing polymer particles (A) to a fibrous material (C) via resin (B), which is not only uneconomical (because of requiring a large amount of heat energy), but also lowers water absorbency and generates of coloring phenomena, which is not desirable.

The melting point of the resin (B) is measured in accordance with JIS K-7196.

The particle size of the resin powder (B) is, in general, 300 μm or smaller, preferably 1–250 μm, and more preferably 10–200 μm. If the particle size exceeds 300 μm, mixtures with the water absorbing polymer particles (A) become nonhomogeneous, and adhesion to fiber degrades; in addition the initial water absorbing rate of the water absorbent is lowered. Furthermore, nonuniform mixtures give rise to the problem of phase separation between the water absorbing polymer particles (A) and the resin (B) during storage, transportation, or use. Moreover a large amount of heat energy is required to allow the water absorbing polymer particles to adhere to the fibrous materials (C) via resin (B), which is not only uneconomical but also lowers the absorbing speed of the water absorbing material produced.

In addition, the resin (B) is preferably a resin which does not dissolve or is not hydrolized even when brought into contact with regular water for 24 hours. This is because when the water absorbing material of the present invention is applied to absorbent articles such as disposable diapers or sanitary napkins, the articles can retain a satisfactory level of adhesion of the water absorbing polymer particles (A) to the fibrous material (C) while they are used, even after urine or menstrual blood is absorbed. On the contraly, if the resin (B) is a resin which dissolves in water after a short time, or becomes soluble in water by hydrolizing,. even though the adhesion between the particles (A) and the fibrous material (C) may be satisfactory in the dry state, the resin dissolves after absorbing urine or menstrual blood, causing a slimy condition or giving rise to problems of displacement or separation of the water absorbed gel.

Examples of fibrous material (C) include cellulose-type fibers, organic synthetic fibers, and mixture of organic synthetic fibers and cellulose type fibers.

Examples of cellulose type fiber include natural fiber such as fluff pulp, cellulose type chemical fiber such as viscose rayon, acetate rayon, and cuprammonium rayon. The raw material of the cellulose-based natural fiber (conifers, broad leaf weeds, etc.), manufacturing method (chemical pulp, semi-chemical pulp, mechanical pulp, CTMP (chemi-thermo mechanical pulp) etc.) and bleaching method are not critical.

Examples of organic synthetic fiber include polypropylene-based fiber, polyethylene-based fiber, polyamide-based fiber, polyacrylonitrile-based fiber, polyester-based fiber, poly(vinyl alcohol)-based fiber, polyurethane-based fiber, thermofusable bicomponent fiber (e.g. bicomponent fibers in which at least two fibers mentioned above, having different melting points are compounded to form the sheath & core type, eccentric core-sheath type or side-by-side type bicomponent fibers, fibers in which at least two types of the above fibers are blended, fibers in which the surface layer of the above fiber is modified, etc.). It is preferable that the lowest melting point of the fiber component is 50°–180° C.

Of the examples of the fibrous material mentioned above, those preferred are cellulose-based natural fiber, polypropylene-based fiber, polyethylene-based fiber, polyester-based fiber, thermofusable bicomponent fiber, and mixture thereof; and particularly preferred are fluff pulp, thermofusable bicomponent fibers and mixtures thereof, because of their excellent shape retaining property of the obtained water absorbing material after water absorption.

The length and thickness of the fibrous materials is not a feature of the invention, but, in general, fibers from 1 to 200 mm longth and from 0.1 to 100 deniers are employed preferably. The form of the fibrous materials also is not critical, provided that it is fibrous; and examples include slender cylindrical-form, split-yarn-form, staple-form, filament-form, web-form, etc.

The ratio of the water absorbing polymer particles (A) to the resin (B) is, in general, 100 parts of the water absorbent polymer (A) to 0.5–30 parts of the resin (B) by weight, preferably, 1–20 parts, and more preferably 3–15 parts. When the amount of the resin (B) exceeds 30 parts by weight, adhesion of the water absorbing polymer particles (A) to a fibrous material (C) is increased, but because the resin (B) covers a large part of the surface of the water absorbing polymer particles (A) (e.g. 80% or more of its area), the absorbing efficiency, absorption speed, and initial absorbing rate of the water absorbent composition, as well as the flexibility of the water absorbing material, are lowered. On the other hand, when the amount of the resin (B) is less than 0.5 parts by weight, not only adhesion of the water absorbing polymer particles (A) to fibrous material (C) lowers, but also the shape-retaining property of water absorbing material after water absorption is degraded.

The weight ratio of the water absorbing polymer particles (A) to the fibrous material (C) is suitably 20:80 to 95:5, preferably 30:70 to 90:10, and more preferably 35:65 to 80:20. When the propotion of the particles (A) is less than 20, the capabilities of the water absorbing material are not thoroughly exhibited, and when it exceeds 95, the shape retaining property of the water absorbing material after water absorption is degraded.

For manufacturing the water absorbent composition comprising the water absorbing polymer particles (A) and the resin (B) of the present invention, mixing the water absorbing polymer particles (A) and the resin (B) in the powder state is the easiest and most economical method. In addition, treating the water absorbing polymer particles (A) and the resin (B) at temperature higher than the temperature exhibit heat adhesion property of the resin (B) after, or simultaneously with mixing the particles (A) and the resin (B), and allowing the resin (B) to partially adhere to the surface of the particles (A) can improve homogeneous mixing and adhesion of the particles (A) and the resin (B) to fiber. It is also possible for the resin (B) to adhere to the surface of the water absorbing polymer particles (A) by a mechanical operation such as hybridization and coatmyzer methods.

The word "partially" used above means that the surface of the water absorbing polymer particles (A) is not completely covered with the resin (B); for example, about 80% or less of the surface area of the water absorbing polymer particles (A), preferably 60–10% of the area, is adhered to by the resin (B). Complete coverage of the water absorbing polymer particles (A) with the resin (B) excessively decreases the water absorption speed and initial absorption rate of the composition.

As the apparatus for mixing of the water absorbing polymer particles (A) with the resin (B), an ordinary powder blender, for example a conical blender, Nauta blender, V-shaped blender, fluidized bed mixer, turbulizer, screw type line blender and honeycomb type static mixer may be used. As apparatus to heat-treat after blending the water absorbing polymer particles (A) and the resin (B), a hot-air heater, Nauta type heater, paddle drier, fluidized bed heater, infrared heater or high-frequency heater may be used. As apparatus to blend and heat the water absorbing polymer particles (A) and the resin (B) simultaneously, a Nauta type heater, paddle drier and fluidized bed heater may be used.

The initial water absorption rate of the water absorbent composition of the present invention is, in general, 40% or more, and preferably 50 % or more. If the initial absorption rate is less than 40%, the water absorbent composition is unsuitable to be applied to sanitary good such as for disposable diapers and sanitary napkins, which must absorb and retain discharged urine or menstrual blood instantaneously. The initial absorption rate is a value measured by a method to be described hereinbelow.

To the water absorbent composition of the present invention, organic powders (e.g., pulp powder, cellulose derivative, natural polysaccharides, etc.) and inorganic powders (e.g., zeolite,fumed silica, alumina, bentonire, activated carbon, etc.), antioxidant, antiseptic agent, disinfectant, surface activate agent, coloring agent, perfume, etc. may be added as extenders and additives, if required. The amount of these agents should be generally 10 weight % or less of the weight of the water absorbent composition.

For the manufacture of the water absorbing material of the present invention, the following methods can be enumerated: (1) prepare a mixture of the water absorbing polymer particles (A) and the resin (B) in advance; then blend the mixture with the fibrous material (C) or spray it over the fibrous material (C) and heat-treat at a temperature exceeding the temperature exhibit heat adhesion property of the resin (B); (2) blend the water absorbing polymer particles (A), the resin (B) and fibrous material (C) in advance, and then heat-treat it at a temperature exceeding the temperature exhibit heat adhesion property of the resin (B); (3) mix the water absorbing polymer particles (A), the resin (B) and fibrous material (C) at a temperature exceeding the temperature exhibit heat adhesion property of the resin (B), so that simultaneously the water absorbing polymer particles (A) are partially adhered to the fibrous material (C); (4) prepare a mixture of the water absorbing polymer particles (A) and the resin (B) in advance, and spray, apply, or affix this mixture to the fibrous material (C) while the temperature of the mixture is held above the temperature exhibit heat adhesion property of the resin (B); (5) melt the resin (B) and spray, apply, or affix it to the fibrous material (C), then sprinkle thereon or mix the water absorbing polymer particles (A); (6) sprinkle or mix a mixture of the water absorbing polymer particles (A) and the resin (B), blended beforehand, to the fibrous material (C) held at a temperature higher than the temperature exhibit heat adhesion property of the resin (B); (7) sprinkle or mix the water absorbing polymer particles (A) and the resin (B) simultaneously or separately on the fibrous material (C) held at a temperature higher than the temperature exhibit heat adhesion property of the resin (B); (8) sprinkle or mix the water absorbing polymer particles (A) heated to a temperature higher than the temperature exhibit heat adhesion property of the resin (B), to a mixture of the resin (B) and the fibrous material (C).

Of these examples of the manufacturing method those preferred are (1) or (6), because a water absorbing material which the water absorbing polymer particles (A) is comparatively uniformly adhered to the fibrous material (C) via the resin (B) can thereby be obtained. The more uniformly the water absorbing polymer particles (A) is adhered to the fibrous material (C) via the resin (B), the better the water absorbing characteristics and the shape retention property after water absorption.

According to the present invention, not all the water absorbing polymer particles (A) are necessarily affixed to the fibrous material (C) via the resin (B). It is sufficient that the water absorbing polymer particles (A) be partially affixed (e.g. 50 weight % or more of the water absorbing polymer particles (A)) to the fibrous material (C). According to favored embodiment, the amount of the resin (B) is increased as much as possible within its prescribed range, or the propotion of fibrous material (C) is increased to increase the contact surface between the water absorbing polymer particles (A) and the fibrous material (C), whereby 60 weight % or more of the water absorbing polymer particles (A) can be adhered to the fibrous material (C). If the adhesion of the water absorbing polymer particles (A) to the fibrous material (C) is less than 50%, then when such water absorbing material is used in sanytary goods such as paper diapers or sanitary napkins, the water absorbing polymer particles (A) may move, become unevenly distributed, become separated or drop out during storage or transportaion of the goods.

As apparatus for mixing of the water absorbing polymer particles (A) and the resin (B) and/or the fibrous material (C), an ordinary blender, for example, conical blender, Nauta blender, V-shaped blender, fluidized bed mixer, or air type blender with or without a spray nozzle for granular substances, and a carding machine for fibrous material equipped with a spray nozzle for granular substances may be used.

As apparatus to heat-treat at a temperature exceeding the temperature exhibits heat adhesion property of the resin (B), suitable examples include hot-air heaters, Nauta type heaters, fluidized bed heaters, air type blenders, heating type calender rolls, infrared heaters, and high-frequency heaters etc.

The water absorbing material of the present invention can be subjected to treatments generally applied to fibrous substances, such as carding, laminating, compressing, cold calendering, heat calendering, needle punching, stretching, paper making process, etc.

To the water absorbing material of the present invention, organic powders (e.g., pulp powder, cellulose derivative, natural polysaccharides, etc.) and inorganic powders (e.g., zeolite, silica, alumina, bentonire and activated carbon, etc.), glass fiber, antioxidant, antiseptic agent, sterilizer or disinfectant, surface activate agent, coloring agent, perfume, etc. may be added as extenders and additives, if required. The amount of these agents should be generally 10 weight % or less, more preferably 5 weight % or less, of the weight of the water absorbing material.

The adhesion coefficient of the water absorbent composition to the fiber, when it is applied to a fibrous material, is generally about 50% or more, under favorable conditions, 60% or more. If the adhesion coefficient of the water absorbent composition to the fiber is less than 50%, then when such composition is used in sanitary goods such as paper diapers or sanitary napkins, the water absorbents may move or become unevenly distributed during storage and transportaion.

Some preferred embodiments of the invention are described in the following Examples and Comparative Examples, but it should be noted that the invention is not limited to these embodiments. The saturated absorption volume, initial absorption rate and adhesion coefficient to the fiber (pulp and/or synthetic fiber) with respect to the water absorbent composition shown in Examples 1–11 and Comparative Examples 1–5 were measured by the following methods. Hereinafter, % represents weight % unless otherwise specified.

Saturated absorption volume 1-g of the water absorbent is charged into a tea bag made of 250-mesh nylon net and immersed in a large excess of 0.9% saline water for 1 hour and to absorb the saline water; it is then removed and drained for 15 minutes by hanging it, and the increased weight is measured. This value is designated the saturated absorption volume (S).

Initial absorption rate 1-g of the water absorbent is charged into a tea-bag made of 250-mesh nylon net and immersed in a large excess of 0.9% saline water for 10 minutes and to absorb the saline water; it is then removed and drained for 15 minutes by hanging it, and the increased weight is measured- This value is designated the saturated absorption volume after 10 minutes (S10).

Initial absorption rate=$(S10/S) \times 100$

Adhesion coefficient to the fiber

A layer of 200 g/m$^2$ fluf pulp or synthetic fiber (ES fiber EA; manufactured by Chisso Corporation) is cut into a 15-cm-diameter disk. Vacuum is applied to the bottom surface of the fiber layer, and 2-g of water absorbent composition is uniformly sprinkled over the disk. Then, after heat-treating it for 2 minutes at a temperature about 10 ° C. higher than the melting point of the resin (B), it is cooled to room temperature and unattached absorbent composition is shaken off. The weight (W) of the water absorbent composition not affixed with the fiber is then measured.

Adhesion coefficient to the fiber=[(2−W)/2]×100 +de

EXAMPLE 1

93 parts of cross-linked sodium acrylate type water absorbing polymer ("SANWET IM-5000D" granular type; Trademark of Sanyo Chemical Industries, Ltd.) and 7 parts of polyethylene modified by maleic acid having grain size of 50–100 μm ("U-mex 2000P", melting point: 108 ° C.; Trademark of Sanyo Chemical Industries, Ltd.) were put into a V-type blender, and was stirre for 20 minutes to obtain the water absorbent (a) of the present invention. The value of its saturated absorption volume, initial absorption rate and adhesion coefficient to the fiber of this water absorbent (a) are shown in Table 1.

EXAMPLES 2 AND 3

The water absorbents (b) and (c) were obtained in the same manner as in Example 1, except that the the mixing ratios of "SANWET IM-5000D" and "U-mex 2000P" were changed as follows:

Water absorbent (b):

["SANWET IM-5000D"]/["U-mex 2000P"]=93/2

Water absorbent (c):

["SANWET IM-5000D"]/["U-mex 2000P"]=80/20

The measurement results of the properties of these water absorbents are shown in Table 1.

EXAMPLES 4 AND 5

The water absorbents (d) and (e) were obtained in the same manner as in Example 1, except that the particle sizes of polyethylene modified by maleic acid were changed as follows:

Grain size of polyethylene modified by maleic acid of water absorbent (d): 10–50 μm.

Grain size of polyethylene modified by maleic acid of water absorbent (e): 150–200 μm.

The measurement results of the properties of these wafer absorbents are shown in Table 1.

EXAMPLES 6, 7 AND 8

The water absorbents (f) through (h) were obtained in the same manner as in Example 1, except that the following resins were used in place of polyethylene modified by maleic acid. The measurement results of the properties of these water absorbents are shown in Table 1.

Water absorbent (f):
Low-molecular polyethlene ("SANWAX 161P", melting point 111° C.; Trademark of Sanyo Chemical Industries, Ltd.)

Water absorbent (g):
Paraffin wax (melting point: 83° C.)

Water absorbent (h):
Polyester type resin ("VYLON GM903P", melting point: 133 ° C.; Trademark of Toyoho Co., Ltd.)

EXAMPLE 9

The water absorbent (j) was obtained by further hot-air-treating the water absorbent (a) obtained in Example 1 at 130° C. for 30 seconds, in which powder of polyethylene modified by maleic acid partially adhered to the surface of the water absorbing polymer particles. The measurement results of the properties of this water absorbent (j) are shown in Table 1.

EXAMPLES 10 AND 11

The water absorbents (k) and (m) were obtained in the same manner as in Example 9, except that the following water absorbing polymers were used in place of "SANWET IM-5000D.":

Water absorbent (k):
Saponified copolymer of vinyl acetate-methyl acrylate ("SUMIKAGEL S-50", pearl like; Trademark of Sumitomo Chemical Co.,Ltd.)

Water absorbent (m):
Copolymer of starch-grafted acrylic acid salt ("SANWET IM-1000", lamellar type; Trademark of Sanyo Chemical Industries, Ltd.)

The measurement results of the properties of these water absorbents are shown in Table 1.

COMPARATIVE EXAMPLES 1–3

Cross-linked sodium acrylate type water absorbing polymer, saponified copolymer of vinyl acetate-methyl acrylate and copolymer of starch-grafted acrylic acid, which are commercially available water absorbing polymers, were used for comparative water absorbents (n)–(p), and the measurement results of saturated absorption volume, initial absorption rate, and adhesion coefficient to the fiber of these water absorbents are shown in Table 1.

COMPARATIVE EXAMPLE 4

The comparative water absorbent (q) was obtained in the same manner as in Example 1, except that the the mixing ratio of "SANWET IM-5000D" to "U-mex 2000P" was changed to 60/40. The measurement results of the properties of the water absorbent are shown in Table 1.

COMPARATIVE EXAMPLE 5

The comparative water absorbent (r) was obtained in the same manner as in the Example 1 disclosed in Japanese Patent Application Laid Open No. 242858/1990, in which the surface of the water absorbing polymer was fully covered with thermoplastic resin. The measurement results of the properties of the water absorbent (r) are shown in Table 1.

TABLE 1

|  | Saturated absorption | Initial absorption | Adhesion cofficient to the fiber (%) | |
| --- | --- | --- | --- | --- |
|  | volume (g/g) | rate (%) | Fluff pulp | Synthetic fiber |
| Example No. | | | | |
| 1 | 47 | 83 | 82 | 87 |
| 2 | 50 | 85 | 52 | 62 |
| 3 | 42 | 76 | 90 | 96 |
| 4 | 48 | 84 | 84 | 90 |

TABLE 1-continued

|  | Saturated absorption volume (g/g) | Initial absorption rate (%) | Adhesion cofficient to the fiber (%) | |
|---|---|---|---|---|
|  |  |  | Fluff pulp | Synthetic fiber |
| 5 | 46 | 81 | 61 | 65 |
| 6 | 46 | 82 | 72 | 76 |
| 7 | 45 | 80 | 70 | 74 |
| 8 | 46 | 83 | 77 | 81 |
| 9 | 47 | 81 | 82 | 85 |
| 10 | 48 | 68 | 74 | 80 |
| 11 | 62 | 72 | 78 | 84 |
| Comparative Example No. | | | | |
| 1 | 48 | 83 | 18 | 22 |
| 2 | 50 | 71 | 9 | 8 |
| 3 | 63 | 72 | 21 | 24 |
| 4 | 28 | 38 | 84 | 92 |
| 5 | 55 | 2 | 83 | 96 |

The following Examples and Comparative Examples are illustrative of the water absorbing material of the invention, but it should again be noted that the invention is not limited to these embodiments alone. The saturated absorption volume, absorbing speed, adhesion rate and shape retention property with respect to the materials shown in Examples 12–24 and Comparative Examples 6–10 were measured by the following methods. Hereinafter, % represents weight % unless otherwise specified.

Saturated absorption volume 1-g of the water absorbing material is charged into a tea-bag made of 250-mesh nylon net and immersed in a large excess of 0.9% saline water for 1 hour to absorb the saline water; it is then removed and drained for 15 minutes by hanging it, and the increased weight is measured. This value is designated as the saturated absorption volume.

Absorption speed 1-g of the water absorbing material is charged into a tea-bag made of 250-mesh nylon net and immersed in a large excess of 0.9% saline water for 2 minutes, then removed and drained for 15 minutes by hanging it. The increased weight is measured and designated as the absorption speed.

Adhesion rate 10-g of the water absorbing material is charged into a 10-mesh sieve (sieve opening: 1.7 mm), then shaken with a Ro-tap type sieve shaker ( manufactured by Iida Seisakusho Co. Ltd.) for 5 minutes. The weight (W) of water absorbing polymer sieved out is measured. Let $W_0$ denote the amount of the water absorbing polymer contained in the water absorbing material before test; the adhesion rate is caluculated from the following equation.

Adhesion rate (%)=[($W_0$−W)/$W_0$]×100

Shape retention property 10 g of water absorbing material is allowed to absorb 200 ml of physiological sodium chloride solution, then placed on a wire gauge of 4-mm mesh size. Vibration is applied to the gauge. The value of the shape retention property of the water absorbing material after absorbing the physiological sodium chloride solution, and the degree of loss of swollen water absorbing resin are observed and evaluated by the following symbols:

U: The shape retention property is good and the water absorbing polymer scarcely drop out at all.

V: The shape retention property is good and the volume of water absorbing resin dropping out is small.

X: The shape is retained to some extent but a large propotion of the water absorbing resin drops out.

Y: The shape is not retained at all and a large propotion of the water absorbing resin drops out.

EXAMPLE 12

93 parts of cross-linked sodium acrylate based water absorbing polymer ("SANWET IM-5000D", granular type; Trademark of Sanyo Chemical Industries, Ltd.) and 7 parts of polyethylene modified by maleic acid having grain size of 50–100 μm ("U-mex 2000P", melting point: 108 ° C.; Trademark of Sanyo Chemical Industries, Ltd.) were placed in a V-type blender and stirred for 20 minutes. Then the mixture and 30 parts of an eccentric type bicomponent fiber ("ES Fiber EA", Trademark of of Chisso Corporation; melting point of low-melting point component: 110 ° C.) and 70 parts of fluff pulp were mixed in an air type blender. Then the mixture was further treated with hot air at 130 ° C. for 2 minutes, and a water absorbing material (A) of the present invention is obtained. The measurement results of saturated absorption volume, absorption speed, adhesion rate and shape retention property of this water absorbing material (A) are shown in Table 2.

EXAMPLES 13 AND 14

The water absorbing material (B) and (C) were obtained in the same manner as in Example 12, except that the mixing ratios of the water absorbing polymer to polyethylene modified by maleic acid were changed as follows:

Water absorbent (B):
  Water absorbing polymer/polyethylene modified by maleic acid=97 parts/3 parts.

Water absorbent (C):
  Water absorbing polymer/polyethylene modified by maleic acid=80 parts/20 parts.

The measurement results of saturated absorption volume, absorption speed, adhesion rate and shape retention property of these water absorbing materials (B) and (C) are shown in Table 2.

EXAMPLES 15–17

The water absorbing material (D) through (F) were obtained in the same manner as in Example 12, except that polyethylene modified by maleic acid was replaced with the same amount of the following resins:

Water absorbent (D):
  Low-molecular polyethylene ("SANWAX 161P" of Sanyo Chemical Industries, Ltd; melting point: 111° C.)

Water absorbent (E):
  Paraffin wax (melting point: 83 ° C.)

Water absorbent (F):
  Polyester type resin ("VYLON GM903P", melting point: 113 ° C.; Toyoho Co., Ltd.)

The measurement results of saturated absorption volume, absorption speed, adhesion rate and shape retention property of these water absorbing materials are shown in Table 2.

EXAMPLES 18–22

The water absorbing material (G) through (M) were obtained in the same manner as in Example 12, except that parts of the bicomponent fiber ("ES Fiber EA", Trademark of of Chisso Corporation; melting point of the low-melting point component: 110 ° $_C$) and 70 parts of fluff pulp were replaced with the following types and volume of fibrous material:

Water absorbing material (G):
60 parts of bicomponent fiber ("ES Fiber EA", Trademark of Chisso Corporation) and 40 parts of fluff pulp.

Water absorbing material (H):
30 parts of bicomponent fiber ("ES Fiber EA", Trademark of Chisso Corporation), 20 parts of polypropylene fiber and 50 parts of fluff pulp.

Water absorbing material (J):
45 parts of bicomponent fiber ("ES Fiber EA", Trademark of Chisso Corporation) and 55 parts of fluff pulp.

Water absorbing material (K):
100 parts of fluff pulp.

Water absorbing material (M):
30 parts of sheath & core type bicomponent fiber ("ES Fiber EAC", Trademark of Chisso Corporation: melting point of the low-melting point component: 110 $a_C$) and 70 parts of fluff pulp.

The measurement results of saturated absorption volume, absorption speed, adhesion rate and shape retention property of this water absorbing material (G) through (M) are shown in Table 2.

EXAMPLE 23

The water absorbing material (N) was obtained in the same manner as in Example 12, except that crosslinked sodium acrylate type water absorbing polymer was replaced with the same volume of the saponified copolymer of vinyl acetate-methyl acrylate ("SUMIKAGEL S-50", pearl like; Trademark of Sumitomo Chemical Co., Ltd.). The measurement results of the properties of the water absorbing material (N) are shown in Table 2.

EXAMPLE 24

93 parts of cross-linked sodium acrylate based water absorbing polymer ("SANWET IM-5000D"; Trademark of Sanyo Chemical Industries, Ltd.) and 7 parts of polyethylene modified by maleic acid having grain size of 50–100 μm ("U-mex 2000P"; Trademark of Sanyo Chemical Industries, Ltd.) were placed in a V-type blender and stirred for 20 minutes. Then the mixture was uniformly sprinkled over 45 parts of the bicomponent fiber ("ES Fiber EA", Trademark of Chisso Corporation), maintained at 130° C., and a water absorbing material (P) in accordance with the present invention was obtained. The measurement results of the properties of this water absorbing material (P) are shown in Table 2.

COMPARATIVE EXAMPLE 6

93 parts of cross-linked sodium acrylate type water absorbing polymer ("SANWET IM-5000D"; Trademark of Sanyo Chemical Industries, Ltd.) and 7 parts of polyethylene modified by maleic acid having grain size of 50–100 μm ("U-mex 2000P"; Trademark of Sanyo Chemical Industries, Ltd.) were placed in a V-type blender and stirred for 20 minutes. Then the mixture and 30 parts of the bicomponent fiber ("ES Fiber EA", Trademark of Chisso Corporation) and 70 parts of fluff pulp were mixed at 25° $_C$ using an air type blender, and a comparative water absorbing material (Q) was obtained. The measurement results of saturated absorption volume, absorption speed, adhesion rate and shape retention property of this comparative water absorbing material (Q) are shown in Table 2.

COMPARATIVE EXAMPLE 7

The water absorbing material (R) was obtained in the same manner as in Comparative Example 6, except that crosslinked sodium acrylate type water absorbing polymer was replaced with the same amount of the saponified copolymer of vinyl acetate-methyl acrylate ("SUMIKAGEL S-50"). The measurement results of the properties of the comparative water absorbing material (R) are shown in Table 2.

COMPARATIVE EXAMPLE 8

The water absorbing material (S) was obtained in the same manner as in Example 12, except that the mixing ratio of the water absorbing polymer to polyethylene modified by maleic acid was changed to 60/40. The measurement results of the properties of the comparative water absorbing material (S) are shown in Table 2.

COMPARATIVE EXAMPLE 9

A dispersion, in which 20 parts of polyethylene modified by maleic acid was dissolved in 180 parts of toluene and then 80 parts of fine powder of cross-linked sodium polyacrylate type water absorbing resin were dispersed, was sprayed over a fibrous material comprising a mixture of 30 parts of bicomponent fiber ("ES Fiber EA", Trademark of Chisso Corporation) and 70 parts of fluff pulp. This was heated and dried at 130° C. to evaporate toluene and to obtain the comparative water absorbing material (T). The measurement results of the properties of the comparative water absorbing material (T) are shown in Table 2.

COMPARATIVE EXAMPLE 10

100 parts of cross-linked sodium polyacrylate type water absorbing polymer ("SANWET IM-5000D"; Trademark of Sanyo Chemical Industries, Ltd.) and 30 parts of the bicomponent fiber ("ES Fiber EA"; Trademark of of Chisso Corporation) and 70 parts of fluff pulp were mixed in an air type blender. Then the mixture was further treated with hot air at 130° C. for 2 minutes, and a comparative water absorbing material (U) was obtained. The measurement results of the properties of the comparative water absorbing material (U) are shown in Table 2.

TABLE 2

| | Saturated absorption volume (g/g) | Absorption speed (g/g) | Adhesion rate (%) | Shape retention property |
|---|---|---|---|---|
| Example No | | | | |
| 12 | 34 | 31 | 92 | U |
| 13 | 36 | 32 | 77 | V |
| 14 | 32 | 26 | 98 | U |
| 15 | 33 | 29 | 85 | V |
| 16 | 33 | 28 | 82 | V |
| 17 | 33 | 29 | 88 | V |
| 18 | 32 | 28 | 96 | U |
| 19 | 31 | 27 | 90 | U |
| 20 | 38 | 32 | 99 | U |
| 21 | 35 | 33 | 83 | V |
| 22 | 34 | 30 | 92 | U |
| 23 | 35 | 27 | 81 | V |
| 24 | 37 | 31 | 86 | V |
| Comparative Example No | | | | |
| 6 | 35 | 28 | 18 | Y |
| 7 | 35 | 25 | 8 | Y |
| 8 | 24 | 9 | 90 | U |
| 9 | 27 | 7 | 93 | X |
| 10 | 35 | 29 | 16 | Y |

The water absorbent composition of the present invention has following features and effects.

① Excellent absorbency, absorption speed and initial absorption rate.

② Excellent adhesion to a fibrous material (e.g., fluff pulp, synthethic fiber web, synthetic fiber filament, nonwoven fbaric, cloth, woven fabric, paper, etc.)

③ Even if it is left in a high-humidity environment, it is free from blocking, in contrast to the behaviour of conventional water absorbing polymer.

④ The water absorbent composition of the present invention can be manufactured in a simple operation by mixing the water absorbing polymer particles (A) with the resin (B).

⑤ Applying the water absorbent composition of the present invention to a fibrous material containing heat adherent fiber, a water absorbing material with excellent shape retention properties after water absorption can be obtained.

The water absorbent composition of the present invention is therefore extremely useful for various sanitary materials, for instance, disposable diapers, sanitary napkins, puerperal mats, medical under pads, etc. It is particularly useful for thinner disposable diapers or thinner sanitary napkins in which the ratio of the water absorbent polymer to fiber (pulp and/or heat adherent fiber) is large.

Furthermore, it is useful for producing freshness retaining materials for fruits and vegetables, drip absorbers for marine foods, water content or moisture control sheets, anti-dewing materials, seedling-raising sheets for rice planting, aging sheets after cementing, and tape-form water absorbing materials such as water sealing materials for communication cables and optical fiber cables,.

In addition, the water absorbing material of the present invention has the following features and effects.

① Excellent absorbency and absorption speed.

② Excellent adhesion to the fibrous material.

③ Good shape retention property even after aqueous solution is absorbed.

④ Even if it is left in a high-humidity environment, it is free from the blocking which is observed with conventional granular water absorbing resin.

⑤ Good workability, including easy blending with other fibers.

The water absorbing material of the present invention is therefore extremely useful for various sanitary materials, for instance, disposable diapers, sanitary napkins, puerperal mats, medical under-pads, etc, and other water-absoptive goods. It is particularly useful for thinner disposable diapers or thinner sanitary napkins in which the ratio of the water absorbent polymer to fiber (pulp and/or heat adherent fiber) is large.

Furthermore, it is useful for producing freshness retaining materials for fruits and vegetables, drip absorbers for marine foods, water content or moisture control sheets, anti-dewing materials, seedling-raising sheets for rice planting, aging sheets after cementing, and tape-form water absorbing materials such as water sealing materials for communication cables and optical fiber cables.

What is claimed is:

1. Water absorbent composition comprising:

(A) water absorbing polymer particles which are capable of absorbing 35 to 100 times of physiological saline solution based on their weight, at least 90% of the polymer particles having a size in the range of 0.1 to 0.9 mm, and (B) powders of at least one resin selected from the group consisting of polyolefin modified by carboxylic acid, olefin-acrylic acid copolymer and copolymer of olefin-maleic anhydride, said resin having a melting point of about 70–180° C. and remaining undissolved and unhydrolyzed after being in contact with water for 24 hours, the powders (B) having a particle size not greater than 300 µm and being present in an amount of 0.5–30 parts by weight per 100 parts by weight of the polymer particles (A).

2. A composition according to claim 1, wherein wherein the amount of the resin powder (B) is 1–20 parts by weight per 100 parts by weight of the polymer particles (A).

3. A composition according to claim 1, whereof the initial water absorption rate is at least 40%.

4. A composition according to claim 1, obtained by heat-treating the polymer particles (A) and resin powder (B), after or during mixing, to render the resin powder (B) partially adherent to the surface of the polymer particles (A).

* * * * *